United States Patent

Adams et al.

[11] Patent Number: 5,868,906
[45] Date of Patent: Feb. 9, 1999

[54] DEHYDRATION AND PURIFICATION OF ISOPROPYL ALCOHOL TO AN ULTRADRY AND ULTRAPURE LEVEL

[75] Inventors: John A. Adams, Escondido; Gerald A. Krulik, San Clemente; Christopher Blatt, La Costa; David Persichini, Oceanside, all of Calif.

[73] Assignee: Athens Corporation, Oceanside, Calif.

[21] Appl. No.: 691,427

[22] Filed: Aug. 2, 1996

Related U.S. Application Data

[63] Continuation of Ser. No. 446,948, May 15, 1995, abandoned.

[51] Int. Cl.⁶ ..................................................... B01D 3/00
[52] U.S. Cl. ..................................... 203/18; 159/DIG. 27; 203/71; 203/DIG. 16; 210/634; 210/774; 210/640; 568/913; 568/916
[58] Field of Search .................... 159/DIG. 27; 202/155, 202/173, 176, 200; 203/DIG. 16, 18, 71; 210/DIG. 6, 634, 640, 295, 774, 664, 650, 767, 799, 806; 568/889, 916, 913, 868

[56] References Cited

U.S. PATENT DOCUMENTS

| | | | |
|---|---|---|---|
| 4,366,032 | 12/1982 | Mikitenko et al. | 203/18 |
| 4,650,574 | 3/1987 | Hilgendorff et al. | 210/640 |
| 4,762,616 | 8/1988 | Litzen et al. | |
| 4,788,043 | 11/1988 | Kagiyama et al. | 210/500.27 |
| 4,879,041 | 11/1989 | Kurokawa et al. | 210/640 |
| 5,053,563 | 10/1991 | Horizoe et al. | |
| 5,091,057 | 2/1992 | Jensen | |
| 5,105,029 | 4/1992 | Ninomiya et al. | 568/872 |
| 5,108,549 | 4/1992 | Wenzlaff et al. | 159/DIG. 27 |
| 5,182,022 | 1/1993 | Pastunak et al. | 159/DIG. 27 |
| 5,217,579 | 6/1993 | Kusakabe et al. | 202/154 |
| 5,248,393 | 9/1993 | Schumacher et al. | |
| 5,250,271 | 10/1993 | Horizoe et al. | |
| 5,360,923 | 11/1994 | Nickel et al. | 568/913 |

FOREIGN PATENT DOCUMENTS

| | | | |
|---|---|---|---|
| 0048427 | 3/1984 | Japan | 568/913 |
| 0856371 | 12/1960 | United Kingdom | 568/913 |
| 2201413 | 9/1988 | United Kingdom | 568/913 |

OTHER PUBLICATIONS

Purified Reagents for Trace Metal Analysis (John R. Moody and Ellyn S. Beary—U.S. National Bureau of Standards, Center for Analytical Chemistry, Inorganic Analytical Research Division. Washington, DC 20234, U.S.A.).

(List continued on next page.)

*Primary Examiner*—Virginia Manoharan
*Attorney, Agent, or Firm*—Knobbe, Martens, Olson & Bear, LLP

[57] ABSTRACT

A method for the on-site reprocessing of isopropyl alcohol used in semiconductor manufacturing, to generate an ultradry and ultrapure isopropyl alcohol. This ultradry and ultrapure isopropyl alcohol is produced through a pervaporation step, followed by double distillation. In the first distillation step, an autonomous azeotropic self-stripping distillation column is used to produce an ultradry and partially purified isopropyl alcohol. In the next step, the isopropyl alcohol is distilled in an overhead product distillation column, to produce an ultrapure and ultradry isopropyl alcohol. Alternatively, if the feed isopropyl alcohol contains less than 2000 ppm water, the pervaporation step may be omitted.

The resulting isopropyl alcohol has between a high of 100 parts per million (ppm) and a low of 0.1 ppm of water in the isopropyl alcohol. It also has zero particles per milliliter of a size larger than 2.0 microns, zero to 2 particles per milliliter of a size of 0.5 micron to 2.0 microns, zero to 30 particles per milliliter of a size between 0.1 microns and 0.5 microns, an unspecified number of particles per milliliter below 0.1 microns, 1 part per trillion (ppt) to 1 part per billion (ppb) of any specific trace impurity such as metals, anions, and cations, and 10 ppt to 10 ppm of any other specific trace organic substances.

7 Claims, 7 Drawing Sheets

OTHER PUBLICATIONS

WACOM IPA Recovery Refinery System (Introduction of IPA Recovery Refinery Function into IPA Vapor Drying System).

Surface Cleanliness—Products in Action—New Drying Technique Controls Watermarks (Circle Reader Service No.346—Microcontamination Aug. 1993).

Kimmon International Fax (Mar. 21, 1994)—Kimmon IPA Vapor Dryers.

Vapor–Liquid Equilibria at 760 Mm. Pressure (Louis H. Ballard and M. Van Winkle—University of Texas, Austin, Texas).

Vapor–Liquid Equilibria—2–Propanol–Water System (Abraham Wilson and Edward L. Simons—Rutgers University, New Brunswick, N.J.).

Ultra–pure IPA Purification and Recycling System (Yukio Yanaga, Mgr., Production Technology and Engineering Ctr, Kurosaki Plant).

Consider Membrane Pervaporation (Hubert L. Fleming, Zenon Environmental, Inc.—Chemical Engineering Progress Jul. 1992).

Carbone Lorraine—Carbone of America (Jun. 9, 1994)—Project #PV7167R1.

S&K Products International Inc. (Jul. 25, 1994)—Model #I.G.–200 IPA Cleaning, Degreasing, Drying System.

SCI Systems, Inc. (Aug. 30, 1994)—Technical Data—IPA High Purity Recycling System—SCI Model 7175.

Mitsubishi Kasei (Sep. 13, 1994)—IPA Vapor Dryer.

Wafer Cleaning (Christopher F. McConnell—Microcontamination Feb. 1991)—Examining the Effects of Wafer Surface Chemistry on Particle Removal Using Direct–Displacement Isopropyl Alcohol Drying.

Ultrapure Chemicals (Alan E. Walter and Christopher F. McConnell—Microcontamination Jan. 1990)—Direct Displacement Wet Processing: How It Affects Wafer Surface Phenomena.

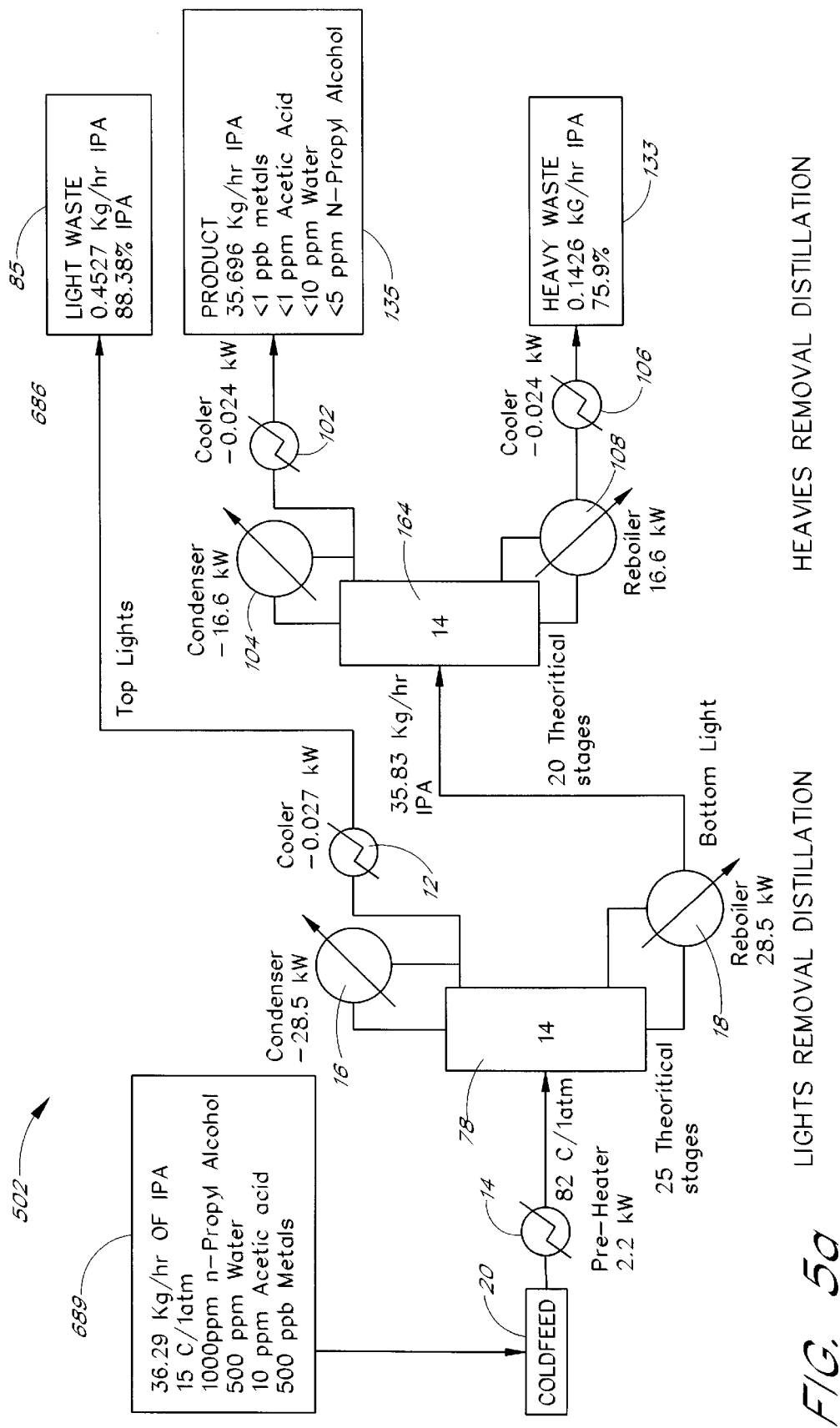
FIG. 5a   LIGHTS REMOVAL DISTILLATION   HEAVIES REMOVAL DISTILLATION

| Item to Control | Sensor Number | Rule | Rule Description |
|---|---|---|---|
| 650 | 632 | 710 | if water content is > 500 ppm slow pump rate |
| 650 | 632 | 712 | if water content < 300 ppm increase pump rate |
| 628 | 630 | 714 | if temperature > T-pervap +10% then decrease flow in valve |
| 628 | 630 | 716 | if temperature < T-pervap -10% then increase flow in valve |
| 658 | 636 | 718 | if temperature > T-Waste +10% then increase flow in valve |
| 658 | 636 | 720 | if temperature < T-Wasate -10% then decrease flow in valve |
| 682 | 638 | 722 | if level > L-Waste +10% then increase pump rate |
| 682 | 638 | 724 | if level < L-Waste -10% then decrease pump rate |
| 28 | 74 | 728 | if temperature > T-preheat +10% then decrease flow in valve |
| 28 | 74 | 730 | if temperature < T-preheat -10% then increase flow in valve |
| 36 | 30 | 732 | if temperature > T-cold-waste +10% then increase flow in valve |
| 36 | 30 | 734 | if temperature < T-cold-waste -10% then decrease flow in valve |
| 38 | 82 | 736 | if concentration < Azeotrope +2% then decrease flow in valve |
| 38 | 82 | 738 | if concentration > Azeotrope +1% then increase flow in valve |
| 58 | 93 | 740 | if pressuredifference > p-light-column +2% then decrease flow in valve |
| 58 | 93 | 742 | if pressure difference < p-light-column -2% then increase flow in valve |
| 58 | 40 | 744 | if absolute pressure > 5 psig then decrease flow in valve |
| 46 | 40 | 746 | if absolute pressure > 2 psig then increase flow in valve |
| 46 | 40 | 748 | if absolute pressure < 1 psig then decrease flow in valve |
| 50 | 66 | 750 | if differential pressure > p-light-boil +5% then increase flow in valve |
| 50 | 66 | 752 | if differential pressure < p-light-boil- 5% then decrease flow in valve |
| 126 | 116 | 754 | if differential pressure > p-heavy-boil +5% then increase flow in valve |
| 126 | 116 | 756 | if differential pressure < p-heavy-boil- 5% then decrease flow in valve |
| 126 | 176 | 758 | if differential pressure > p-heavy-column +5% then decrease flow in valve |
| 126 | 176 | 760 | if diffeerential pressure < p-heavy-column- 5% then increase flow in valve |
| 148 | 95 | 762 | if differential pressure > p-light-heavy+ 5% then decrease flow in valve |
| 148 | 95 | 764 | if differential pressure < p-light-heavy- 5% then increase flow in valve |
| 148 | 144 | 766 | if absolute pressure > 1 psig then increase flow in valve |
| 148 | 144 | 768 | if absolute pressure < 0.5 psig then decrease flow in valve |
| 142 | 80-172 | 770 | if flow rate of 80 minus rate of 172> flow rate measured by 174 + 1% then increase flow in valve |
| 142 | 80-172 | 772 | if flow rate of 80 minus ate of 172 < flow rate measured by 174 - 1% then decrease flow in valve |
| 136 | 154 | 774 | if temperature > T-product +5% then increase flow in valve |
| 136 | 154 | 776 | if temperature < T-product- 5% then decrease flow in valve |

FIG. 6

DEHYDRATION AND PURIFICATION OF ISOPROPYL ALCOHOL TO AN ULTRADRY AND ULTRAPURE LEVEL

This application is a continuation of U.S. patent application Ser. No. 08/446,948 filed May 15, 1995, abandoned.

BACKGROUND OF THE INVENTION

This invention relates generally to an apparatus and method for purification and dehydration of isopropyl alcohol. More particularly, the present invention relates to a method and apparatus suitable for location at a semiconductor manufacturing facility and useful for continuous on-site dehydration and purification of isopropyl alcohol to ultradry and ultrapure levels.

Many steps in the semiconductor wafer manufacturing process are followed by a deionized water rinse, which is then followed by a drying step. During this wafer drying step, it is important to prevent watermarks from forming on the surface of the silicon wafers. Watermarks typically form when silicon dioxide and other dissolved contaminants precipitate out of the deionized water as it evaporates from the surface of the wafer. The presence of watermarks on a partially manufactured wafer creates serious difficulties in subsequent manufacturing processes.

Watermark formation on silicon wafers can be minimized or prevented by keeping the deionized water from evaporating off of the wafer surface during the drying process. Several important techniques for achieving this result involve the use of isopropyl alcohol (IPA). In one such technique, the water on the surface of the wafer is displaced by isopropyl alcohol before the water has a chance to evaporate, and then the alcohol is evaporated from the surface of the wafer. Another technique, called vapor drying, involves condensation of isopropyl alcohol vapor onto the surface of the wafer, causing the water present on the wafer to be taken up by the dry alcohol. The water-rich alcohol then drips off of the wafer before water evaporation can occur, and is replaced by more dry alcohol condensate, which is then evaporated.

To minimize or prevent watermarks and to enhance drying, semiconductor manufacturers prefer using ultrapure and ultradry isopropyl alcohol. Ultrapure is defined here as having zero particles per milliliter of a size larger than 2.0 microns, having zero to 2 particles per milliliter of a size of 0.5 microns to 2.0 microns, having zero to 30 particles per milliliter of a size between 0.1 microns and 0.5 microns, having an unspecified number of particles per milliliter below 0.1 microns, having 1 part per trillion (ppt) to 1 part per billion (ppb) of any specific trace impurity such as metals, anions, and cations, and having 10 ppt to 10 parts per million (ppm) of any other specific trace organic substances. Ultradry is defined here as having between a high of 100 parts per million (ppm) and a low of 0.1 ppm of water in the isopropyl alcohol.

Currently, the availability of ultradry and ultrapure isopropyl alcohol from suppliers is limited in relation to the demands of the industry for the chemical. In addition, ultrapure and ultradry isopropyl alcohol purchased from offsite suppliers may lose its purity due to contaminants or water added during its handling and transportation to the semiconductor manufacturer. Moreover, transporting thousands of liters of hazardous chemicals over public highways every month is undesirable.

Even if a semiconductor manufacturer is fortunate enough to secure an adequate supply of ultrapure and ultradry isopropyl alcohol, once the chemical is used to dry semiconductor wafers and picks up contamination and water, it is no longer useful as a drying agent and must be disposed of. In the past, this has involved resale to industries demanding less pure isopropyl alcohol, or disposal as a hazardous chemical, or sending the isopropyl alcohol off-site for recycling. All of these disposal methods create additional expenses for the semiconductor manufacturer, which are passed on to consumers in the form of higher prices.

The best solution to these problems is for the semiconductor manufacturer to recycle and purify the used isopropyl alcohol to an ultrapure and ultradry level at the manufacturing facility. Unfortunately, the current methods of purifying and dehydrating isopropyl alcohol are not suited to meet this need. For example, one well-known method of purifying isopropyl alcohol involves simple overhead product distillation. This method, while useful in removing contaminants with boiling points higher than isopropyl alcohol, cannot be used to dehydrate isopropyl alcohol to an ultradry level, because isopropyl alcohol forms a low boiling azeotrope with water. In addition, this method also does nothing to remove those contaminants with boiling points lower than isopropyl alcohol.

Another method used to dehydrate isopropyl alcohol involves use of pervaporation membranes. Pervaporation membranes can be used to dry isopropyl alcohol with a high initial water content to water levels around 300 to 500 ppm. It is extremely difficult, however, to use pervaporation to dehydrate isopropyl alcohol to an ultradry level having a water content of less than 100 ppm. Moreover, depending upon the type of pervaporation membrane used, pervaporation may actually add particles and organic materials to the isopropyl alcohol. Thus, pervaporation, by itself, cannot be used to recycle used isopropyl alcohol to an ultrapure and ultradry level.

Another method teaches the use of a molecular sieve to dehydrate the isopropyl alcohol, followed by overhead product distillation for purification. The combination of the molecular sieve process and distillation, however, does nothing to remove most light organic substances or other contaminants with low boiling points. Thus, while this method can work better than previous methods in achieving ultradry isopropyl alcohol, contaminants with boiling points lower than isopropyl alcohol may still remain after treatment.

Another prior art method teaches the process of adding a second liquid to an alcohol-water mix, such as propane as described in U.S. Pat. No. 5,053,563, or di-isopropyl ether as described in U.S. Pat. No. 4,762,616. The second liquid is added because it forms a lower boiling point azeotrope with water than the azeotrope of isopropyl alcohol and water. Two column distillation is then used to break the isopropyl alcohol-water azeotrope and dehydrate the alcohol. While this process might work for isopropyl alcohol, the complexity of the process makes it difficult for use as an on-site recycling process for use at semiconductor manufacturing sites. In addition, the use of a second liquid raises serious questions regarding the possible introduction of additional impurities.

For the foregoing reasons, there is a need for a method and apparatus, suitable for location at a semiconductor manufacturing facility, which can be used to recycle isopropyl alcohol to ultradry and ultrapure levels at the cost and volumes needed by the semiconductor manufacturing industry.

SUMMARY OF THE INVENTION

The present invention is directed to a method and apparatus that satisfies the need of the semiconductor manufacturer for dehydrating and purifying used isopropyl alcohol to an ultradry and ultrapure level.

In accordance with one aspect of the present invention, there is provided a method for dehydrating and purifying a solution containing isopropyl alcohol, water, and minor amounts of other contaminants to produce an ultradry and ultrapure isopropyl alcohol. The first step of this method involves removing water from a solution containing isopropyl alcohol by pervaporation of the solution through a water-permeable membrane. This produces a partially dehydrated isopropyl alcohol solution which contains a small amount of water, and minor amounts of other contaminants. The next step is to distill the partially dehydrated isopropyl alcohol in an autonomous azeotropic self-stripping distillation column, to remove substantially all of the remaining water and low boiling point contaminants, thereby producing an ultradry and partially purified isopropyl alcohol which is removed from a reboiler at the column bottom. The next step in the method involves distilling the ultradry and partially purified isopropyl alcohol through a low-boiling overhead product distillation column, then taking the ultradry and ultrapure isopropyl alcohol as an end product overhead condensate.

The advantages of the method of the present invention are that it provides a relatively simple process to recycle used isopropyl alcohol to an ultrapure and ultradry level, allowing less complicated and lower cost equipment to be installed at the semiconductor manufacturing facility. Furthermore, the method of the present invention is adapted to work with isopropyl alcohol solutions having wide variations in water content, so that even if the isopropyl alcohol solution is severely contaminated with water, the present method can be used to dehydrate and purify it. The present method also avoids the need for the addition of a second chemical to break the isopropyl alcohol-water azeotrope.

In accordance with another aspect of the present invention, there is provided a method of dehydrating and purifying an isopropyl alcohol solution containing only minor amounts of organic and inorganic contaminants, and less than about 2,000 ppm water, to an ultrapure and ultradry level. In this embodiment, the solution to be dehydrated and purified is not passed through a pervaporation membrane, as discussed previously, but is instead first introduced into an autonomous azeotropic self-stripping distillation column. This first distillation step removes substantially all of the water and low boiling point contaminants from the isopropyl alcohol solution, to produce an ultradry and partially purified isopropyl alcohol which is removed from a reboiler at the column bottom. The next step involves distilling the ultradry and partially purified isopropyl alcohol through a low-boiling overhead product distillation column, then taking the ultradry and ultrapure isopropyl alcohol as an end product overhead condensate.

Preferably, in each described distillation step used in practicing the methods of the present invention, the distillation column will have from 11 to 40 theoretical distillation plates. In addition, in the preferred methods of the present invention, the ultrapure and ultradry isopropyl alcohol end product is subsequently filtered to remove submicron sized particulate impurities.

In another aspect of the present invention, there is provided an apparatus which can be used to practice the above-described methods. An apparatus having the features of the present invention comprises an isopropyl alcohol input line which is connected to a pervaporation chamber, or to other means for pervaporation of an isopropyl alcohol solution. An output line from the pervaporation chamber is attached to a first distillation system, which comprises a preheating column connected to an autonomous azeotropic self-stripping distillation column, where the distillation column includes a condenser at its top, and a reboiler at its bottom. The reboiler of the distillation column has an output line which is adapted to permit removal of an ultradry and partially purified isopropyl alcohol product after the distillation process has occurred. The output from this reboiler is connected to a second distillation system which comprises a low boiling overhead product distillation column. This second distillation column has a reboiler at its bottom, and an end product condenser at its top. A product cooling column connected to the end product condenser is used to cool the distilled ultrapure and ultradry isopropyl alcohol after the distillation, and the end product then passes into an end product output line connected to the cooling column.

In accordance with another aspect of the present invention, there is provided an apparatus useful for deydrating and purifying isopropyl alcohol solutions containing less than about 2000 ppm water. The apparatus of this embodiment features an isopropyl alcohol input line which is attached to a first distillation system. The first distillation system comprises a preheating column connected to an autonomous azeotropic self-stripping distillation column, where the distillation column includes a condenser at its top, and a reboiler at its bottom. The reboiler of the distillation column has an output line adapted to permit removal of an ultradry and partially purified isopropyl alcohol product after the distillation process has occurred. The output from this reboiler is connected to a second distillation system which comprises a low boiling overhead product distillation column. This second distillation column has a reboiler at its bottom, and an end product condenser at its top. A product cooling column connected to the end product condenser is used to cool the distilled ultrapure and ultradry isopropyl alcohol after the distillation, and the end product then passes into an end product output line connected to the cooling column.

Preferably, the distillation columns of the preferred embodiments of the present invention are constructed in such a manner that they comprise 11 to 40 theoretical plates. In addition, in the preferred embodiments of the present invention, filtration means are connected to the end product output line to remove any submicron sized particulate impurities passed through the filtration means.

These and other features and advantages of the present invention will become apparent from the detailed description of the preferred embodiments which follows, when taken together with the attached drawings and claims.

BRIEF DESCRIPTION OF THE DRAWINGS

FIG. 5a shows the process flow diagram of the preferred apparatus used in accordance with the method and process of the present invention for the conditions given in example 1.

FIG. 6 shows a set of control rules which may be executed by hardware and software controllers which can be used in the present invention.

DETAILED DESCRIPTION OF PREFERRED EMBODIMENTS

In one preferred embodiment, the method according to the present invention for dehydrating and purifying isopropyl alcohol to an ultradry and ultrapure level begins with pervaporation of a solution containing isopropyl alcohol, water, and minor amounts of various other contaminants, thereby producing an impure and partially dehydrated isopropyl alcohol containing about 500 ppm water. The isopropyl alcohol from the pervaporation step is then channeled to a first distillation step, where the partially dehydrated isopropyl alcohol is distilled in an autonomous azeotropic self-stripping distillation column to remove substantially all of the remaining water and other low-boiling contaminants, thereby forming an ultradry isopropyl alcohol. The ultradry isopropyl alcohol from the first distillation step is then channeled to a second distillation step, to remove impurities with boiling points higher than isopropyl alcohol, thereby forming an ultrapure and ultradry isopropyl alcohol product. Optionally, a filtration step may be added after the second distillation step to further purify the ultrapure and ultradry isopropyl alcohol.

In another preferred embodiment of the present invention, applicable when the isopropyl alcohol to be purified and dehydrated contains less than 2000 ppm water, no pervaporation step is used in the dehydration process. In this embodiment, the isopropyl alcohol solution to be purified and dehydrated is directly channeled to the first distillation step where the isopropyl alcohol is distilled in an autonomous azeotropic self-stripping distillation column to remove substantially all of the water and other low-boiling contaminants, thus forming an ultradry alcohol. The ultradry alcohol from the first distillation step is then channeled to a second distillation step, to remove impurities with boiling points higher than isopropyl alcohol, thereby forming an ultrapure and ultradry isopropyl alcohol product. optionally, a filtration step may be added after the second distillation step to further purify the ultrapure and ultradry isopropyl alcohol.

Another preferred embodiment of the present invention is an apparatus, small enough to be located at a semiconductor manufacturing facility, and capable of practicing the methods of the present invention to purify and dehydrate isopropyl alcohol to an ultrapure and ultradry level.

Figure 1:
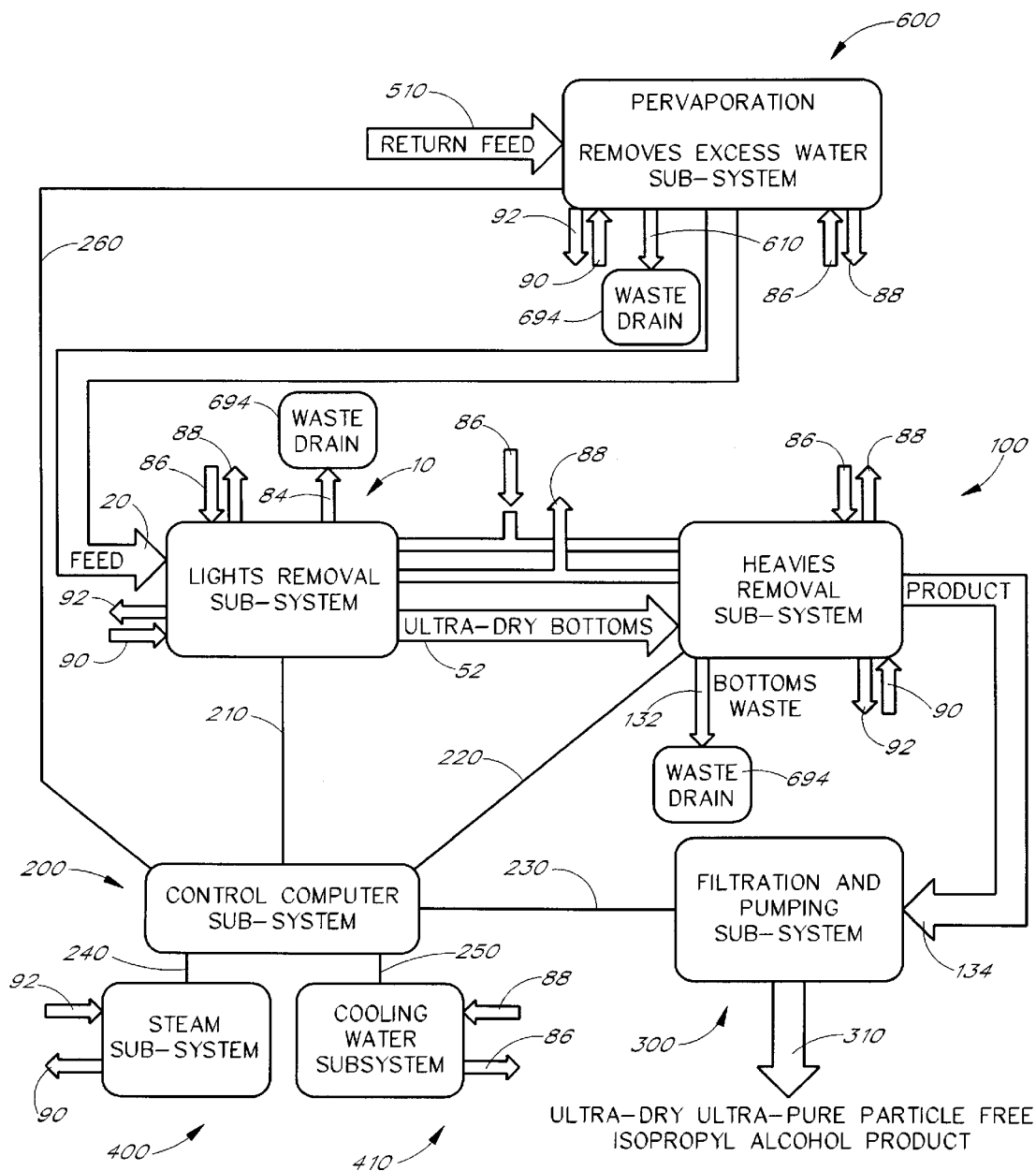
FIG. 1 shows a block diagram of the preferred apparatus used in accordance with the method of the present invention.
Figure 2:
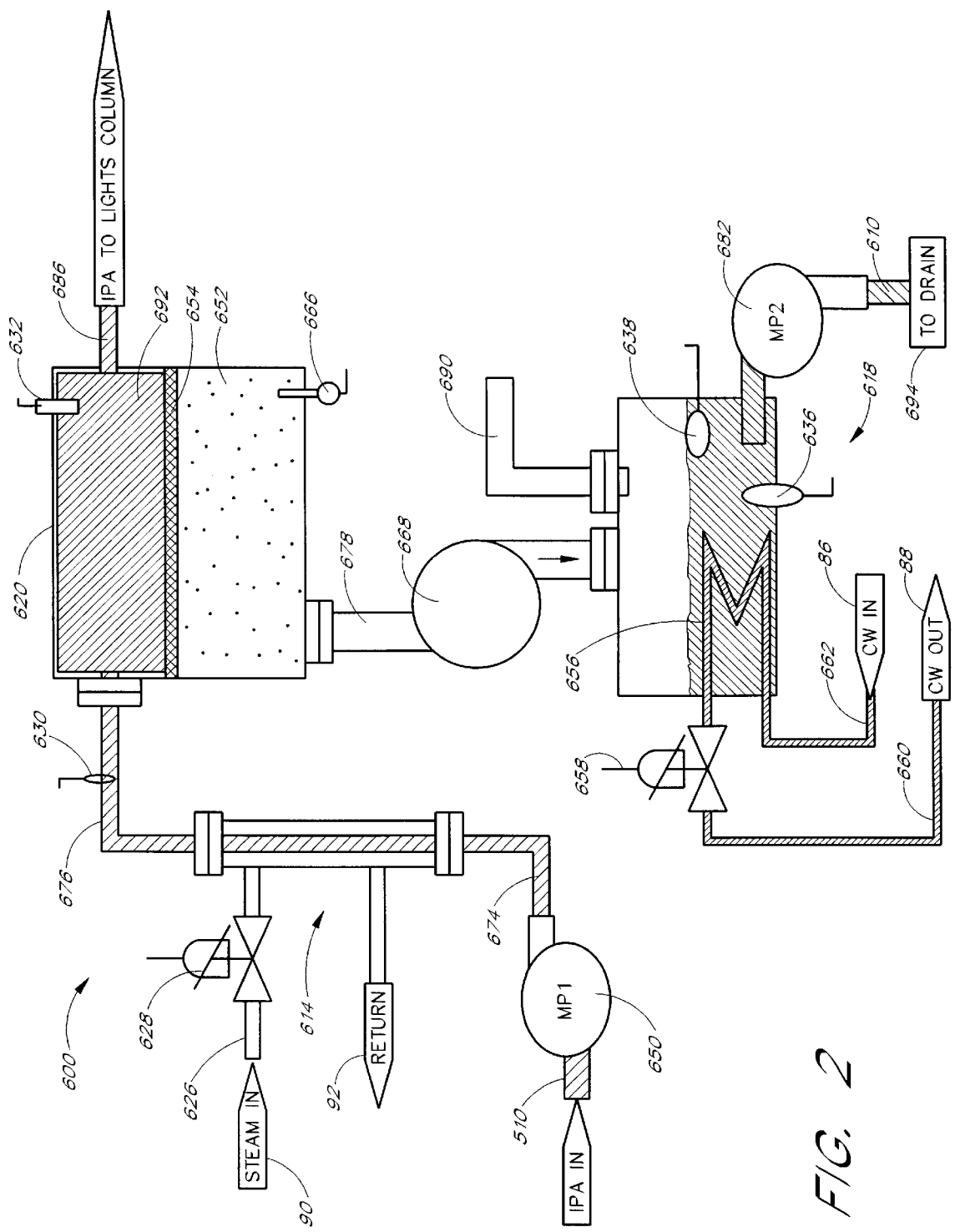
FIG. 2 is a schematic diagram of the preferred apparatus used to practice the pervaporation step of the invention.

FIGS. 1 and 2 disclose a representation of a preferred embodiment of an apparatus suitable for carrying out the pervaporation step of the present invention. The pervaporation step of the present invention removes the excess water from the isopropyl alcohol, producing a partially dehydrated isopropyl alcohol containing about 500 ppm water. Pervaporation is especially advantageous when the isopropyl alcohol to be dehydrated contains water in excess of the azeotropic concentration, as conventional distillation is ineffective in separating the water-isopropyl alcohol azeotrope.

Referring now to FIG. 2, the pervaporation sub-system 600 comprises a pre-heater column 614, a pervaporation cell 620, a pervaporation vacuum apparatus 668, and a pervaporation waste water condenser 618. Isopropyl alcohol to be processed, containing from 0.2% to 12% by weight water, plus from 1 ppm to 3% other impurities, enters the pervaporation feed line 510, passes through metering pump 650, and flows into the pervaporation pre-heater column 614. Preferably, pre-heater column 614 heats the isopropyl alcohol to a temperature of about 50 degrees Celsius, thereby optimizing the removal of water during the subsequent pervaporation. Heat is supplied to the pre-heater column 614 from a steam source line 90 through a feed line 626. The steam flow through pre-heater column 614 is controlled by an inlet steam control valve 628, thereby permitting the regulation of the temperature of pre-heater column 614. The resulting steam condensate passing through pre-heater column 614 exits through a condensate return line 624 to a steam return line 92, for recycling through the steam sub-system 400. After being heated within the pre-heater column 614, the isopropyl alcohol flows through a pervaporation cell feed line 676 and into the pervaporation cell 620. Preferably, a thermocouple 630 is positioned on the feed line 676 to facilitate temperature measurements of the heated isopropyl alcohol before it is input into the pervaporation cell 620.

Pervaporation cell 620 comprises a pervaporation dehydration chamber 692, a pervaporation vaporate chamber 652, and a water permeable pervaporation membrane 654, where the pervaporation membrane 654 separates the pervaporation dehydration chamber 692 from the pervaporation vaporate chamber 652. In the most preferred embodiment, the pervaporation membrane 654 is highly permeable to water, but substantially impermeable to isopropyl alcohol. Advantageously, the atmospheric pressure of pervaporation chamber 652 is reduced relative to the pervaporation dehydration chamber 692 to facilitate diffusion of water across pervaporation membrane 654, and its subsequent evaporation in the pervaporation vaporate chamber 652. In the illustrated embodiment, this is achieved by vacuum apparatus 668 which is attached to the pervaporation vaporate chamber 652 by vacuum line 678. In practice, the pervaporation cell 620 removes water from isopropyl alcohol because the pervaporation membrane 654 is both permeable to water and has a greater chemical affinity for water than for isopropyl alcohol. Thus, water molecules entering into the pervaporation dehydration chamber 692 adhere to the pervaporation membrane 654, then diffuse across the membrane and evaporate from the membrane into pervaporation vaporate chamber 652.

Water vapor passing through the pervaporation membrane 654 condenses in the pervaporation vaporate chamber 692, and is subsequently drawn into vacuum line 678 to be deposited in a waste water condenser 618. Preferably, a vacuum sensor 666 is positioned within the pervaporation vaporate chamber 692 to facilitate measurement of the level of vacuum created by the vacuum apparatus 668. The water in the waste water condenser 618 is removed from the pervaporation sub-system by a metering pump 682, and is delivered to a waste drain 694 through the waste water line 610. Cooling water enters into the waste water condenser 618 through a cooling water input line 662, flows through condenser coil 656, and exits through a cooling water output line 660. The flow of cooling water through condenser coil 656 is controlled by a water control valve 658. Optionally, a thermocouple 636 can be positioned within the waste water condenser 618 to facilitate measurement of the waste water temperature. Also optionally, a level sensor 638 can be positioned within pervaporation waste water condenser 618 to facilitate measurement of the waste water level. In the embodiment illustrated in FIG. 2, an exhaust 690 is required for proper operation.

Isopropyl alcohol which is partially dehydrated in the pervaporation dehydration chamber 692 flows from the pervaporation cell 620 through a pervaporation sub-system output line 686 to distillation subsystem 10 for further processing. Optionally, in a more preferred embodiment, a water content monitor 632 is positioned within the pervaporation dehydration chamber to facilitate the measurement of the isopropyl alcohol water content. The water content monitor 632 may be an automatic concentration gauge based upon the dielectric constant of the isopropyl alcohol, or it may be an automatic Karl Fisher Titrator that determines the water content directly, or any other concentration monitoring means one skilled in the art may employ.

Pervaporation units suitable for practicing the present invention are well known in the art, and may be easily manufactured or obtained from a variety of suppliers. For example, a complete pervaporation unit suitable for practicing the present invention, called the MiniPervap plant, may be purchased from Carbone of America, Parsippany, N.J.

Figure 3:
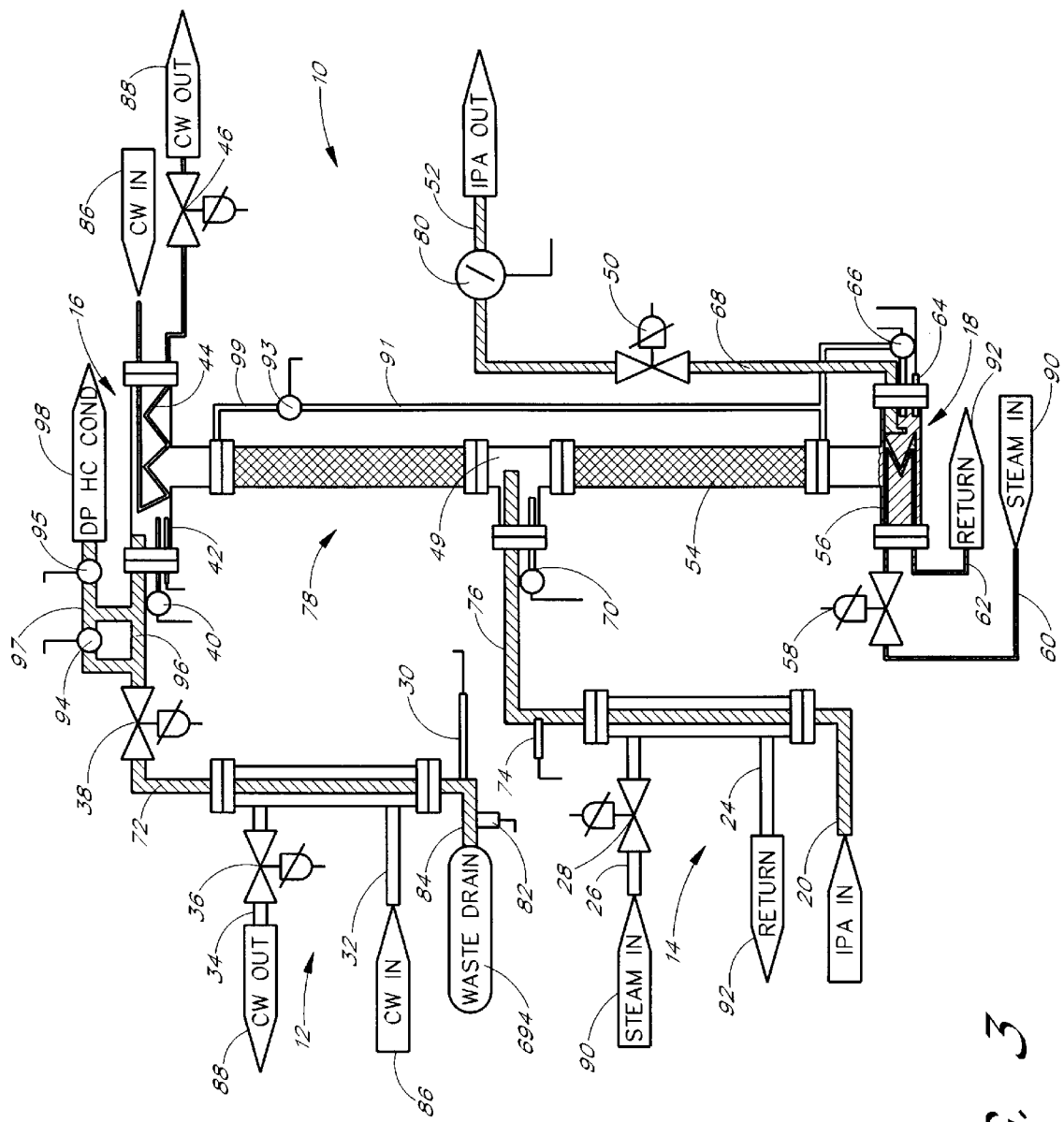
FIG. 3 is a schematic diagram of the preferred apparatus used to practice the first distillation step of the method of the present invention.

FIGS. 1 and 3 illustrate the details of a preferred embodiment of an apparatus suitable for carrying out the first distillation step of the present invention. The first distillation step removes water remaining after the pervaporation step, bringing the isopropyl alcohol to an ultradry level of between 0.1 ppm to 100 ppm water. Alternately, if the starting isopropyl alcohol contains less than 2000 ppm water, the pervaporation step may be bypassed, and the isopropyl alcohol may be introduced directly into the first distillation step.

Referring to FIG. 3, the first distillation sub-system 10 comprises a pre-heater column 14, an autonomous azeotropic self-stripping distillation column 78, a reboiler 18, a condenser 16, a waste product cooler 12, and a reboiler output line 68.

Isopropyl alcohol from the pervaporation step of the present invention, containing approximately 500 ppm of water and various other multi-ppm level contaminants, flows through a feed line 20 into the pre-heater column 14. Alternately, in an embodiment of the present invention bypassing the pervaporation step, isopropyl alcohol containing less than 2000 ppm water is input directly into feed line 20 where it flows to the pre-heater column 14. Preferably, the preheater 14 column heats the isopropyl alcohol to a temperature of about 82 degrees Celsius, thereby allowing the distillation process to begin immediately upon the introduction of the isopropyl alcohol into distillation column 78. Steam from the steam source line 90 passes through a steam feed line 26, and provides a heating source for the pre-heater column 14. The steam flow is controlled by the inlet steam control valve 28, and the resulting steam condensate exits through the condensate return line 24 to the steam return line 92, for recycling in the steam sub-system 400.

The heated isopropyl alcohol flows through the preheater column 14, into column feed line 76, and into distillation column 78. Preferably, a thermocouple 74 is positioned on the feed line 76 to facilitate temperature measurements of the isopropyl alcohol before it flows into the distillation column 78. The distillation column 78 uses high efficiency packing to provide from eleven to forty theoretical plates in the compact vertical space. Preferably, distillation column 78 is packed such that it has twenty theoretical plates. More preferably, distillation column 78 is packed such that it has twenty-five theoretical plates. In the twenty-five plate embodiment, the isopropyl alcohol is introduced into the distillation column 78 preferably at a point corresponding to theoretical plate number fourteen out of twenty-five. The rectifying section 48 and the stripping section 54 of distillation column 78 provide for the separation of water and other low-boiling point contaminants from the isopropyl alcohol. Preferably, a differential pressure sensor 93 is positioned on a differential pressure column line 99, where column line 99 is connected to the reboiler 18 and the top and bottom of the distillation column 78, as illustrated in FIG. 3, to facilitate measurement of the pressure across the distillation column 78.

The distillation column reboiler 18 provides a receptacle for fluids refluxing through the distillation column 78. Liquids in the reboiler 18 are heated by heat transfer from a reboiler steam coil 56. Steam coil 56 receives steam from a feed line 60, which in turn is connected to the steam source line 90. The flow of steam through steam coil 56 is controlled by a steam inlet control valve 58, which permits adjustment of the reboiler temperature by varying steam flow. Steam passing through the steam coil 56 condenses, and the resulting steam condensate flows through condensate return line 62 and into steam return line 92. Preferably, a differential pressure sensor 66 and a thermocouple 64 are positioned within the reboiler 18 to facilitate temperature and pressure measurements of the fluid within the reboiler. A reboiler output line 68 is provided in reboiler 18 to withdraw the ultradry isopropyl alcohol after the distillation process. Passing through reboiler outlet line 68, the ultradry isopropyl alcohol is sent to column output line 52 for delivery to the second distillation subsystem 100. A control valve 50 and feed flowmeter 80 are used to regulate the flow of the ultradry isopropyl alcohol into the second distillation sub-system 100.

Distillation column condenser 16 is situated on top of the distillation column 78. Cooling water from the water source line 86 flows into the condensing coil 44 within the column condenser 16, causing the condensation of gaseous vapors rising up through the distillation column 78, for proper reflux back into column rectifying section 48. The cooling water exits condensing coil 44, flowing through a condenser outlet water control valve 46 and into the water return line 88, eventually returning to a cooling water subsystem 410, which recycles cooling water for reuse system-wide. Preferably, a thermocouple 42 and a pressure sensor 40 are positioned within the condenser 16 to facilitate measurement of pressure and temperature. Also preferably, a differential pressure sensor 95 is positioned on an inter-column differential pressure line 98, where pressure line 98 connects distillation column 78 to distillation column 164, depicted in FIG. 4, to provide pressure measurements between the condenser 16 and a second distillation column condenser 104, also shown in FIG. 4 The conduit piping for differential pressure sensor 97 is used to provide pressure commutation to the pressure gauges.

Distillation waste product consisting of vapors of the isopropyl alcohol, water, and other contaminants with boiling points lower than isopropyl alcohol, pass through condenser 16 and into waste output line 72. Preferably, a differential pressure sensor 94 and a flow restrictor 96 are positioned on waste output line 72 to provide mass flow information for the column waste output line 72. Vapor waste flow through waste output line 72 is regulated by control valve 38, and waste vapors are directed to a waste product cooler 12, where they are cooled and condensed into liquid form. Cooling water from the water source line 86 flows into the waste product cooler 12 through an inlet water line 32. The flow of cooling water is controlled by the outlet water control valve 36. After passing through waste product cooler 12, the water is returned to the water return line 88 through the outlet water line 34. The resulting cool waste product passes through waste line 84 to be stored and subsequently sent for off-site recycling. Preferably, a thermocouple 30 and a water concentration sensor 82 are positioned on waste line 84 to facilitate measurement of the temperature and water concentration of the waste product. The concentration sensor 82 may be an automatic concentration gauge based upon the dielectric constant of the isopropyl alcohol, or it may be an automatic Karl Fisher Titrator that determines the water content directly, or any other concentration monitoring means one skilled in the art may employ.

Figure 4:
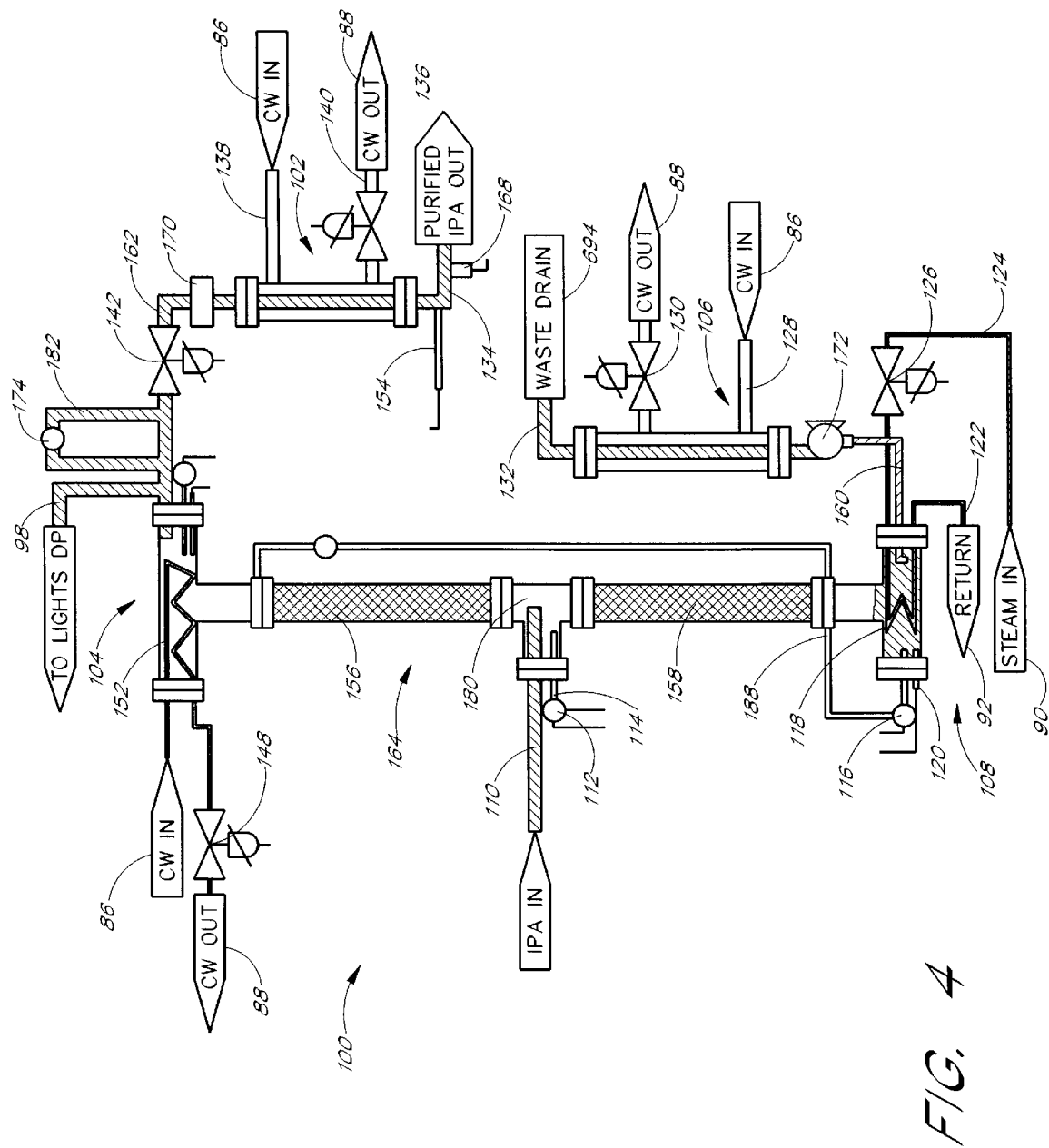
FIG. 4 is a schematic diagram of the preferred apparatus used to practice the second distillation step of the method of the present invention.

FIGS. 1 and 4 illustrate the details of the preferred embodiment of an apparatus suitable for carrying out the second distillation step of the present invention. In this step, the isopropyl alcohol is brought to an ultrapure level of zero particles per ml. larger than 2 microns, zero to 2 particles per ml. from 0.5 to 2 microns, zero to 30 particles per ml. from 0.1 to 0.5 microns, and unspecified number of particles less than 0.1 microns. The final product may contain any specific trace impurity, such as metals, cations, anions at levels from approximately 1 ppt to less than 1 ppb, and any other specific trace organic substances may be present at levels from 10 ppt to less than 10 ppm.

Referring now to FIG. 4, second distillation subsystem 100 comprises a distillation column 164, a condenser 104, a reboiler 108, a reboiler waste product output line 160, a waste product cooler 106, and an end product cooler 102. Ultradry isopropyl alcohol from the first distillation subsystem 10, containing less than 100 ppm water and minor amounts of various high-boiling point contaminants, flows through a feed line 110 into the distillation column 164. Distillation column 164 uses high efficiency packing to provide from eleven to forty theoretical plates in the compact vertical space. Preferably, the distillation column 164 is packed such that it has twenty theoretical plates. In the twenty-plate embodiment, the isopropyl alcohol from the first distillation step is preferably introduced into distillation column 164 at point corresponding to theoretical plate number fourteen out of twenty. The rectifying section 156 and stripping section 158 of distillation column 164 provide for the separation needed. Preferably, a pressure sensor 112 and a thermocouple 114 are positioned on the distillation column 164 near the isopropyl alcohol input point to facilitate the measurement of the pressure and temperature of the fluid within the distillation column 164.

The distillation column reboiler 108 provides a receptacle for fluids refluxing through the distillation column 164. The column reboiler 108 is heated by heat transfer from the reboiler steam coil 118. Steam coil 118 receives steam from a feed line 124, which in turn is connected to steam source line 90. Steam inlet control valve 126 controls the flow of steam through steam coil 118. Advantageously, adjustment of inlet control valve 126 allows for temperature regulation of the reboiler 108. Steam passing through steam coil 118 condenses, and the resulting steam condensate flows through the condensate return line 122 and into the steam return line 92. Preferably, a differential pressure sensor 116 is positioned on reboiler pressure line 188, where pressure line 188 connects the bottom of the distillation column 164 and the reboiler 108, to measure pressure differences. Also preferably, a thermocouple 120 is positioned within the reboiler 108 to facilitate temperature measurements of the fluid within the reboiler. A reboiler output line 160 is provided in the reboiler 108 to withdraw the waste product, consisting of isopropyl alcohol and various high boiling contaminants. Passing through the reboiler output line 160, the waste flows through purge flow metering pump 172, and into waste product cooler 106, where it is cooled and then channeled into the waste drain 694 for off-site recycling.

Distillation column condenser 104 is situated on top of the distillation column 164. Cooling water from the water source line 86 flows into the condensing coil 152 within the column condenser 104, causing the condensation of gaseous vapors rising up through the column, for proper reflux back into column rectifying section 156. The cooling water exits condensing coil 152 through the condenser outlet water control valve 148 flowing to the water return line 88. Preferably, a thermocouple 146 and pressure sensor 144 are positioned with the condenser 104 to facilitate measurement of pressure and temperature.

Distillation end product, consisting of the vapor of ultrapure and ultradry isopropyl alcohol, passes through condenser 104 and into vapor product output line 162. Vapor product flow valve 142 regulates the flow of product into the vapor product output line 162. Preferably, a differential pressure sensor 174 and a flow restrictor 178 are positioned on vapor product output line 162 to provide mass flow information for the vapor product output line 162. Ultrapure and ultradry isopropyl alcohol vapor flows through the vapor product output line 162 to a vapor phase particle filter 170, which filters the isopropyl alcohol vapor to remove various contaminants distilled along with the isopropyl alcohol. After filtration in the vapor phase particle filter 170, the gaseous ultrapure and ultradry isopropyl alcohol enters the end product cooler 102, where it is cooled and condenses into liquid form. Cooling water flows into the end product cooler 102 through a inlet water line 138 from the water source line 86. The flow of cooling water is controlled by the outlet water control valve 136, and after passing through end product cooler 102, the water flows through outlet water line 140 into the water return line 88. The resulting cool ultrapure and ultradry isopropyl alcohol end product then passes through liquid product output line 134. Preferably, a thermocouple 154 and a water content monitor 168 are positioned on liquid product output line 134 to facilitate measurement of the temperature and water concentration of the ultrapure and ultradry isopropyl alcohol. The water content monitor 168 may be an automatic concentration gauge based the automatic Karl Fisher Titrator that determines the water content directly, or any other concentration monitoring means one skilled in the art may employ. For the very low level of water content expected, a concentration monitor based upon the dielectric constant of the isopropyl alcohol is not preferred here.

In one preferred embodiment, illustrated in block diagram form in FIG. 1, the cooled ultrapure and ultradry isopropyl alcohol is then sent to filtration and pumping subsystem 300, through the end product output line 134, for additional filtration. The final product is then transported through a system isopropyl alcohol output line 310 to storage facilities for later use, or directly to the semiconductor manufacturing process.

In another preferred embodiment, also illustrated in FIG. 1, a computer control system 200 monitors and controls all aspects of the process through electrical and signal connections to the various parts of the system. Thus, for example, the computer controls the first distillation subsystem 10 through data communication and control instructions passing through data computer conduit 210. Similarly, the second distillation sub-system 100 is controlled through computer conduit 220, the filtration and pumping sub-system 300 through computer conduit 230, the steam sub-system 400 through computer conduit 240, the Control single line with cooling water sub-system 410 through computer conduit 250, and the pervaporation sub-system 600 through computer conduit 260.

With respect to the computer controlled embodiment, FIG. 6 shows a set of control rules which may be executed by the various hardware and software controllers present within the system. The set of control rules comprise a list of items to control, a list of sensors providing control reference data, and a list of english description of control rules.

Metering pump 650 is controlled by using data provided by a pervaporation water content monitor 632 through rules 710 and 712. These rules provide for steady water concentration of the partially dehydrated isopropyl alcohol to output line 686. If the water content increases, then the pump is slowed down to allow more time for the pervaporation cell 620 to remove water.

Inlet steam control valve 628 is controlled by using data provided by a thermocouple 630 through the rules 714 and 716. These rules keep the temperature of the liquid in feed line 676 within the desired operating temperature range.

Water control valve 658 is controlled by using data provided by a thermocouple 636 through the rules 718 and 720. These rules keep the temperature of liquid in the waste water line 610 within the desired operating temperature range.

Metering pump 682 is controlled by using data provided by the level sensor 638 through rules 722 and 724. These rules keep the level of the liquid within the pervaporation waste water condenser 618 within the desired operating range.

Inlet steam control valve 28 is controlled by using data provided by thermocouple 74 through rules 728 and 730. These rules keep the temperature of the liquid in feed line 76 within the desired operating temperature range.

Outlet water control valve 36 is controlled by using data provided by a thermocouple 30 through rules 732 and 734. These rules keep the distillation waste 85 within the desired operating temperature range.

Control valve 38 is controlled by using data provided by concentration sensor 82 through the rules 736 and 738. These rules keep the concentration of distillation waste 85 slightly above the azeotropic concentration of isopropyl alcohol, thus ensuring most of the remaining water has been stripped from the liquid in feed line 76.

Reboiler inlet steam control valve 58 is controlled by using data provided by the differential pressure sensor 93 through rules 740 and 742. These rules keep the heat input to reboiler 18 at the proper setting to ensure proper boilup.

Reboiler inlet steam control valve 58 is also controlled by using data provided by pressure sensor 40 through rule 744. This rule prevents pressure runaway in column condenser 16.

Outlet water control valve 46 is controlled by using data provided by pressure sensor 40 through rules 746 and 748. These rules allow for proper regulation of column condenser 16.

Feed control valve 50 is controlled by using data provided by differential pressure sensor 66 through rules 750 and 752. These rules allow for proper flow of the ultradry isopropyl alcohol through output line 52 into feed line 110, and also prevent reboiler 18 from overfilling.

Inlet steam control valve 126 is controlled by using data provided by the differential pressure sensor 116 through rules 754 and 756. These rules keep the heat input to reboiler 108 at the proper setting to ensure proper boilup.

Inlet steam control valve 126 is also controlled by using data provided by differential pressure sensor 176 through rules 758 and 760. These rules keep the heat input to reboiler 108 at the proper setting to ensure proper boilup.

Outlet water control valve 148 is controlled by using data provided by the differential pressure sensor 95 through rules 762 and 764. These rules allow for proper regulation of column condenser 104.

Outlet water control valve 148 is also controlled by using data provided by pressure sensor 144 through rules 766 and 768. These rules allow for proper regulation of column condenser 104.

Control valve 142 is controlled by using data calculated from the mass flow data provided by feed flowmeter 80 minus the mass flow data from the purge flow metering pump 172 and compared to the mass flow data measured by the differential pressure sensor 174 through rules 770 and 772. These rules allow for proper material flow through the removal column 164.

Outlet water control valve 136 is controlled by using data calculated from thermocouple 154 through the rules 774 and 776. These rules keep the temperature of the liquid in product output line 134 within the desired operating temperature range.

Accordingly, the reader will see that we have invented a simpler and better method and process, allowing less complicated and lower cost equipment to be installed on-site at semiconductor manufacturing factories, for obtaining ultrapure and ultradry isopropyl alcohol.

Although the description of our invention contains many specificities, these should not be construed as limiting the scope of the invention but as merely providing illustrations of some of the presently preferred embodiments of this invention. For example, the high boiling contaminants could be removed first and the light boiling contaminants removed in the second distillation step of the process. The method and process as embodied in the preferred apparatus could be carried out in batch form of pervaporation and batch distillation steps, even allowing for the elimination of the second column, since the light contaminants could be removed first, then the same column could be used to purify the remaining dry isopropyl alcohol to ultrapure levels by taking the overhead condensate after the light impurities have been removed. Also, other preferred flow rates could allow a larger or smaller apparatus to be built employing the method and process of our invention.

Thus, the scope of the invention should be determined by the appended claims and their legal equivalents, rather than by the examples given.

EXAMPLE 1

FIG. 5a shows the flow diagram of the preferred apparatus used in accordance with the process of the present invention for the conditions given below. Example 1 illustrates the use of the invention when the feed to the system contains less than a few thousand parts per million water content and therefore does not require a pervaporation stage to remove most of the water from the feed.

An isopropyl alcohol solution containing 1000 ppm n-propyl alcohol, approximately 500 ppm water, 10 ppm acetic acid, and 500 ppb metals, at 15 degrees Celsius is enters feed line 20 at a rate of approximately 36.29 kg/hr. The solution is then conducted to the pre-heater column 14 where it is heated to 82 degrees Celsius with approximately 2.2 KW of heat supplied by the pre-heater column 14.

The heated isopropyl alcohol solution then enters distillation column 78 at a point corresponding to theoretical plate number fourteen out of twenty-five plates total. A light waste 85, consisting of approximately 88% isopropyl alcohol and any light boiling contaminants, is removed from the distillation column 78 at a rate of 0.4527 kg/hr with the use of 0.027 kW of cooling supplied to the waste product cooler 12 while 28.5 kW of cooling is supplied to the column condenser 16 to provide high level reflux of condensate back to the distillation column 78. 28.5 kW of heat is required in the column reboiler 18 to drive the first column.

35.83 kg/hr of now ultra-dry isopropyl alcohol is removed from the distillation column 78 and enters into distillation column 164 at a point corresponding to theoretical plate number fourteen out of twenty total theoretical plates. A heavy waste 133, consisting of approximately 75.9% isopropyl alcohol is sent to waste at a rate of 0.1425 kg/hr after being cooled by 0.024 kW of cooling supplied to the waste product cooler 106. Approximately 16.6 kW of heat is required in the column reboiler 108 to drive the second column.

The desired ultradry and now ultrapure isopropyl alcohol is delivered at a rate of approximately 35.696 kg/hr as the ultrapure and ultradry product 135, after it is cooled by 0.024 kW of cooling supplied to the end product cooler 102. The column condenser 104 supplies a high level of reflux for the removal column 164 when supplied with cooling of 16.6 kW. The overall efficiency of the two column distillation in this example is calculated to be 98.36% recovery of isopropyl alcohol.

EXAMPLE 2

Figure 5B:
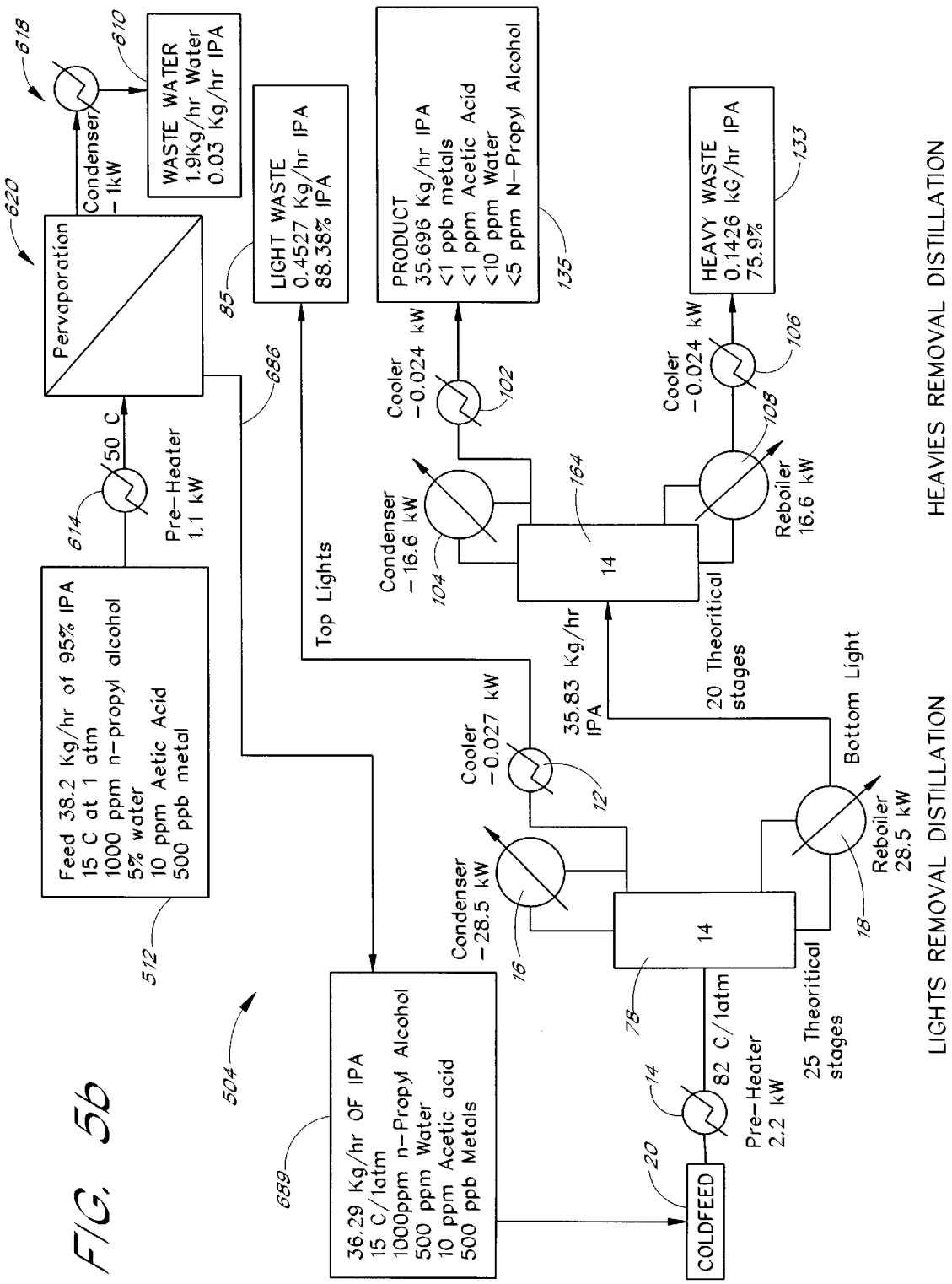
FIG. 5b shows the process flow diagram of the preferred apparatus used in accordance with the method and process of the present invention for the conditions given in example 2.

FIG. 5b shows the flow diagram of the preferred apparatus used in accordance with the process of the present invention for the conditions given below. Example 2 illustrates the use of the invention when the feed to the system contains more than a few thousand parts per million water content and therefore requires a pervaporation stage to remove most of the water from the feed.

An isopropyl alcohol solution containing approximately 1000 ppm n-propyl alcohol, 5% water, 10 ppm acetic acid, and 500 ppb metals, at approximately 15 degrees Celsius enters the pre-heater column 614 at a rate of 38.2 kg/hr where it is heated to 50 degrees Celsius with 1.1 kW of heat, and then enters the pervaporation cell 620. The pervaporation waste water condenser 618 removes approximately 1.9 kg/hr of a waste water from pervaporation condenser line 610. The waste water contains no more than 0.03 kg/hr of isopropyl alcohol.

Partially dehydrated isopropyl alcohol containing 1000 ppm n-propyl alcohol, approximately 500 ppm water, 10 ppm acetic acid, and 500 ppb metals, at 50 degrees Celsius exits the pervaporation sub-system 600 through output line 686 and enters the feed line 20 at a rate of approximately 36.29 kg/hr. The partially dehydrated isopropyl alcohol is then conducted to the pre-heater column 14 where it is heated to 82 degrees Celsius with approximately 1.1 KW of heat supplied to the pre-heater column 14.

The heated isopropyl alcohol enters the distillation column 78 at point corresponding to theoretical plate number fourteen out of twenty-five total. A light waste 85, consisting of approximately 88% isopropyl alcohol and any low boiling contaminants, is removed from the distillation column 78 at a rate of 0.4527 kg/hr with the use of 0.027 kW of cooling supplied to the waste product cooler 12. A total of 28.5 kW of cooling is supplied to the column condenser 16 to provide a high level reflux of condensate back to the distillation Column 78. A total of 28.5 kW of heat is required in the column reboiler 18 to drive the first column.

Ultradry isopropyl alcohol is removed from distillation column 78 at the rate of 35.83 kg/hr, and enters the distillation column 164 at a point corresponding to theoretical plate number fourteen of twenty total theoretical plates. A heavy waste 133, consisting of approximately 75.9% of isopropyl alcohol is sent to waste at a rate of 0.1425 kg/hr after being cooled by 0.024 kW of cooling supplied to the waste product cooler 106. Approximately 16.6 kW of heat are required in the column reboiler 108 to drive the second column.

The desired ultradry and now ultrapure isopropyl alcohol end product is delivered at a rate of approximately 35.696 kg/hr after it is cooled by 0.024 kW of cooling supplied to the end product cooler 102. The column condenser 104 supplies a high level of reflux for the distillation column 164 when supplied with cooling of 16.6 kW. The overall efficiency of the two column distillation in this example yields a 98.36% recovery of isopropyl alcohol.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. A method of dehydrating and purifying an impure aqueous solution of isopropyl alcohol, resulting in an ultrapure and ultradry isopropyl alcohol, said method comprising the steps of:

removing water from an impure aqueous solution of isopropyl alcohol, containing approximately 0.2 to 12% water by weight, by pervaporation of the isopropyl alcohol solution through a water permeable membrane to produce a partially dehydrated isopropyl alcohol containing less than 2000 ppm water by weight;

removing substantially all of the remaining water and any organic substances with boiling points less than isopropyl alcohol from the partially dehydrated isopropyl alcohol by a first distillation in a stripping first distillation column, wherein any said organic substances and water are removed by distilling the organic substances with boiling points less than isopropyl alcohol and an isopropyl alcohol/water azeotrope as overhead product, thereby producing a partially purified and ultradry isopropyl alcohol; and subjecting the ultradry and partially purified isopropyl alcohol to a second distillation through a low boiling overhead product second distillation column, and taking an ultradry and ultrapure isopropyl alcohol end product as overhead product, wherein the ultrapure and ultradry isopropyl alcohol end product contains less than about 100 parts per million water, zero particles per milliliter of a size greater than two microns, less than two particles per milliliter of a size greater than 0.5 microns, less than about thirty particles per milliliter of a size less than 0.5 micron but greater than 0.1 micron, less than about 1 part per billion of any specific anion or cation, and less than about ten parts per million of any specific organic substance with a boiling point different from isopropyl alcohol.

2. The method of claim 1, wherein the first distillation column comprises eleven to forty theoretical distillation plates.

3. The method of claim 1, wherein the second distillation column comprises eleven to forty theoretical distillation plates.

4. The method of claim 1, further comprising filtering the ultrapure and ultradry isopropyl alcohol end product to remove submicron sizes of particulate matter.

5. A method of dehydrating and purifying impure isopropyl alcohol, resulting in an ultrapure and ultradry isopropyl alcohol, said method comprising the steps of:

removing substantially all water and any organic impurities with boiling points less than isopropyl alcohol from an isopropyl alcohol solution containing less than about 2000 parts per million water by a first distillation in a stripping distillation column, wherein any said organic substances and water are removed by distilling the organic substances with boiling points less than isopropyl alcohol and an isopropyl alcohol/water azeotrope as overhead product, thereby producing a partially purified and ultradry isopropyl alcohol;

subjecting the ultradry and partially purified isopropyl alcohol to a second distillation through a low boiling overhead product distillation column, and taking an ultradry and ultrapure isopropyl alcohol end product as overhead product, and filtering the ultrapure and ultradry isopropyl alcohol end product to remove submicron sizes of particulate matter, such that said ultrapure and ultradry isopropyl alcohol end product contains less than about 100 parts per million water, zero particles per milliliter of a size greater than two microns, less than two particles per milliliter of a size greater than 0.5 microns, less than about thirty particles per milliliter of a size less than 0.5 micron but greater than 0.1 micron, less than about 1 part per billion of any specific anion or cation, and less than about ten parts per million of any specific organic substance with a boiling point different from isopropyl alcohol.

6. The method of claim 5, wherein the first distillation column comprises eleven to forty theoretical distillation plates.

7. The method of claim 5, wherein the second distillation column comprises eleven to forty theoretical distillation plates.

* * * * *